(12) United States Patent
Kar et al.

(10) Patent No.: US 10,876,197 B2
(45) Date of Patent: *Dec. 29, 2020

(54) SURFACE MODIFIED MATERIALS FOR TAILORING RESPONSES TO ELECTROMAGNETIC FIELDS

(75) Inventors: Aravinda Kar, Oviedo, FL (US); Rajan Vaidyanathan, Oviedo, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,730

(22) Filed: May 21, 2012

(65) Prior Publication Data

US 2012/0296350 A1 Nov. 22, 2012

Related U.S. Application Data

(60) Provisional application No. 61/488,320, filed on May 20, 2011, provisional application No. 61/613,807, filed on Mar. 21, 2012, provisional application No. 61/615,683, filed on Mar. 26, 2012.

(51) Int. Cl.

| | |
|---|---|
| *C23C 10/00* | (2006.01) |
| *C23C 10/02* | (2006.01) |
| *C23C 10/48* | (2006.01) |
| *A61L 31/14* | (2006.01) |
| *A61L 27/30* | (2006.01) |
| *A61L 29/10* | (2006.01) |
| *A61L 27/50* | (2006.01) |
| *A61L 29/14* | (2006.01) |
| *A61L 31/08* | (2006.01) |
| *C23C 18/08* | (2006.01) |
| *C23C 18/06* | (2006.01) |
| *C23C 18/14* | (2006.01) |
| *A61B 17/00* | (2006.01) |
| *A61N 1/375* | (2006.01) |
| *A61N 1/37* | (2006.01) |
| *A61B 90/00* | (2016.01) |
| *A61N 1/08* | (2006.01) |

(52) U.S. Cl.
CPC ............ *C23C 10/00* (2013.01); *A61L 27/306* (2013.01); *A61L 27/50* (2013.01); *A61L 29/106* (2013.01); *A61L 29/14* (2013.01); *A61L 31/088* (2013.01); *A61L 31/14* (2013.01); *C23C 10/02* (2013.01); *C23C 10/48* (2013.01); *C23C 18/06* (2013.01); *C23C 18/08* (2013.01); *C23C 18/143* (2019.05); *A61B 2017/00911* (2013.01); *A61B 2090/3954* (2016.02); *A61L 2420/02* (2013.01); *A61N 1/086* (2017.08); *A61N 1/375* (2013.01); *A61N 1/3718* (2013.01); *A61N 1/37512* (2017.08); *Y10T 428/24802* (2015.01); *Y10T 428/265* (2015.01)

(58) Field of Classification Search
None
See application file for complete search history.

(56) References Cited

U.S. PATENT DOCUMENTS

| | | | | |
|---|---|---|---|---|
| 4,374,669 | A | * | 2/1983 | MacGregor ...................... 419/9 |
| 5,554,178 | A | * | 9/1996 | Dahl et al. .................... 607/122 |
| 5,744,958 | A | * | 4/1998 | Werne .......................... 324/318 |
| 6,506,972 | B1 | | 1/2003 | Wang |
| 6,805,898 | B1 | * | 10/2004 | Wu et al. ..................... 427/2.25 |
| 10,358,723 | B2 | | 7/2019 | Vaidyanathan et al. |
| 2002/0183629 | A1 | | 12/2002 | Doacher et al. |
| 2004/0140945 | A1 | * | 7/2004 | Werner .............. H01Q 15/0086 343/909 |
| 2005/0153145 | A1 | | 7/2005 | Yamashita et al. |
| 2008/0195186 | A1 | | 8/2008 | Li et al. |
| 2008/0262625 | A1 | | 10/2008 | Spriano et al. |
| 2008/0274671 | A1 | * | 11/2008 | O'Donoghue et al. ......... 451/39 |
| 2009/0035448 | A1 | * | 2/2009 | Flanagan et al. ............ 427/2.24 |

(Continued)

FOREIGN PATENT DOCUMENTS

| | | |
|---|---|---|
| CN | 101356119 A | 1/2009 |
| GB | 1124684 A | 8/1968 |

(Continued)

OTHER PUBLICATIONS

Ewald A., et al., "Antimicrobial titanium/silver PVD coatings on titanium", 2006, Biomedical Engineering Online, pp. 1-10.*
Sintering, "Sintering", accessed from: http://en.wikipedia.org/wiki/Sintering; accessed on Jun. 15, 2014; pp. 1-14.*
Largeanu, A., et al., "Pulsed Laser Deposition of Ni Thin Films on Metallic Substrate ", U.P.B. Sci. Bull. A., Jan. 2011, pp. 195-202.*
Z. Tian, et al., "Laser-enhanced diffusion of nitrogen and aluminum dopants in silicon carbide", Acta Materialia, vol. 54 (2006), pp. 4273-4283, published by Elsevier Ltd.

(Continued)

*Primary Examiner* — Michael G. Hartley
*Assistant Examiner* — Lance W Rider
(74) *Attorney, Agent, or Firm* — Allen, Dyer, Deppelt + Gilchrist, PA

(57) ABSTRACT

A composition of matter includes a substrate material (M) having a bulk portion and an outer surface integrated to the bulk portion. The outer surface includes a modified surface layer. The modified surface layer extends to a depth from the outer surface of at least 1 nm. The modified surface layer includes M and at least one other material (X) which is a metal or metal alloy. The modified surface layer has a 25° C. electrical conductivity which is at least 2.5% above or below a 25° C. electrical conductivity in the bulk portion of M. The composition of matter can be an article that includes a frequency selective surface-based metamaterial, and the plurality of modified surface portions can be a plurality of periodic surface elements that provide a resonant frequency.

18 Claims, 5 Drawing Sheets

(56) References Cited

U.S. PATENT DOCUMENTS

| | | | |
|---|---|---|---|
| 2009/0043378 A1 | 2/2009 | Cheng et al. | |
| 2009/0118822 A1* | 5/2009 | Holman | A61L 31/022 623/1.49 |
| 2009/0123733 A1* | 5/2009 | Ohrlander et al. | 428/328 |
| 2009/0126627 A1* | 5/2009 | Quick | H01L 21/76838 118/620 |
| 2009/0156411 A1 | 6/2009 | Sohma et al. | |
| 2010/0055494 A1 | 3/2010 | Gillesberg et al. | |
| 2010/0057179 A1* | 3/2010 | Storey | 607/119 |
| 2010/0279023 A1* | 11/2010 | Kusinski | C23C 4/08 427/455 |
| 2011/0015756 A1* | 1/2011 | Pawar | A61L 27/04 623/23.53 |
| 2011/0034983 A1 | 2/2011 | Min et al. | |
| 2012/0040102 A1 | 2/2012 | Meredith | |
| 2014/0061909 A1* | 3/2014 | Speckels et al. | 257/741 |

FOREIGN PATENT DOCUMENTS

| | | |
|---|---|---|
| JP | 1994176916 | 6/1994 |
| JP | 2004209275 | 7/2004 |
| JP | 2006278753 | 10/2005 |
| JP | 2006176916 | 7/2006 |
| JP | 2008230880 | 10/2008 |
| JP | 2009537248 A | 10/2009 |

OTHER PUBLICATIONS

Sachin Bet, et al., "Effect of laser field and thermal stress on diffusion in laser doping of SiC", Acta Materialia, vol. 55 (2007), pp. 6816-6824, published by Elsevier Ltd.

Schuh et al., Mechanical behavior of amorphous alloys. Acta Materialia 55(2007) 4067-4109, Elsevier Ltd.

Nace International, Intergranular Corrosion, https://www.nace.org/Corrosion-Central/Corrosion-101/Intergranular-Corrosion/.

Callister, Jr. et al., Materials Science and Engineering an Introduction, 9th Edition, Chapter 3 The Structure of Crystalline Solids, pp. 84-85 and 92-93, Wiley.

A Kar, et al., "One-Dimensional Finite-Medium Diffusion Model for Extended Solid Solution in Laser Cladding of Hf on Nickel", Acta Metall., vol. 36, No. 3, pp. 701-712, 1988.

* cited by examiner

SURFACE MODIFIED MATERIALS FOR TAILORING RESPONSES TO ELECTROMAGNETIC FIELDS

CROSS REFERENCE TO RELATED APPLICATIONS

This application claims the benefit of Provisional Application Ser. No. 61/488,320 entitled "SURFACE MODIFICATION OF MATERIALS FOR TAILORING RESPONSES TO ELECTROMAGNETIC FIELDS" filed May 20, 2011, Provisional Application Ser. No. 61/613,807 entitled "EFFECTS OF POLARIZATION ON LASER DIFFUSION AND MATERIALS MODIFICATION" filed Mar. 21, 2012, and Provisional Application Ser. No. 61/615,683 entitled "SURFACE MODIFICATION OF MATERIALS FOR TAILORING RESPONSES TO ELECTROMAGNETIC FIELDS" filed, Mar. 26, 2012, which are all herein incorporated by reference in their entireties.

FIELD

Disclosed embodiments relate to materials including particles and articles having modified surfaces which provide a modified overall response to incident electromagnetic fields as compared to the bulk of the material.

BACKGROUND

Magnetic Resonance Imaging (MRI) is a medical imaging technique commonly used to image inside the human body. Generally a strong magnetic field (e.g., 1.5 T) is applied to the patient to align the nuclear magnetization vectors of hydrogen atoms in the water of the tissue of the patient under investigation. Simultaneously a RF (e.g., 63.86 MHz) magnetic field (~0.14 µT) is applied to perturb the aligned magnetization, causing the hydrogen nuclei to emit energy signatures that are detectable by a scanner in the MRI system.

The MRI signal is used to construct an image. Different tissues are detected because the protons in various tissues return to their equilibrium nuclear magnetization states at different rates. This effect is used to create contrast among different types of tissues. Diseased tissues, such as tumors, can be detected in this manner as well.

A time-varying magnetic field creates an electric field within any electrically conductive material and the electric field, in turn, induces an electric current, referred to as the "eddy current". Generally the electromagnetic field penetrates into metals up to a certain depth, commonly associated referenced to a "skin depth". An electromagnetic wave entering a conducting surface is damped so that the current density is largest near the surface of the conductor and reduces in amplitude by a factor 1/e at a distance δ from the surface given by:

$$\delta = [2/(\omega \mu_0 \sigma)]^{1/2}$$

where ω is the angular frequency of the radiation, and σ is the electrical conductivity of the metal. The distance δ is referred to as the skin depth of the conductor, and it can be seen if the electrical conductivity (σ) increases, the skin depth (δ) decreases. For example, at 60 Hz in copper, the skin depth is about 8.5 mm. At high frequencies the skin depth may be much smaller (shallower).

The eddy current can heat up the conductive material by the Joule effect and this process is called induction heating. Induction heating can cause thermal damage to tissues while conducting MRI scans for patients wearing implants that have leads, such as in spinal fusion stimulators, cardiac pacemakers and neurostimulation systems. A maximum temperature change of 25.38° C. has been reported for a deep brain stimulation implant shortly after initiating MRI. The heating can be more severe at metal tips. A temperature elevation of 63.18° C. has been reported to have occurred at the tip of a pacing electrode (unattached to a cardiac pacing pulse generator) within 90 s of initiating MRI.

There is thus a need for new materials that provide surfaces which generate reduced MRI-induced induction heating. Although selection of a conventional high electrical conductivity metal material can reduce MRI-induced induction heating somewhat by reducing the amount of energy that is actually introduced into the material via the skin effect, the resulting MRI-induced induction heating may still be too high for certain applications.

SUMMARY

Disclosed embodiments recognize MRI-induced induction heating of implants and subsequent heating of surrounding tissues are not just affected by the electrical conductivity of the material, but can also be significantly affected by other thermophysical and electromagnetic properties (e.g., permittivity, permeability, absorption, transmission, reflectivity, density, specific heat capacity and thermal conductivity, heat transfer from the heated material to the surrounding tissues). For example, there may be very little penetration of the magnetic field into the material but that limited penetration can still result in a large amount of heating over a small volume that can damage human tissue. Conversely, there may be substantial penetration of the magnetic field into the material, but the heating may be spread over a larger volume so that the heating is reduced overall and there is thus less damage to human tissue. In this regard, disclosed embodiments recognize that the thermophysical properties (e.g., density, specific heat capacity and thermal conductivity) can be relevant to MRI-induced induction heating in addition to the electrical conductivity of the material. The thermophysical and electromagnetic properties of the material in turn can influence its mechanical properties (stiffness, strength, fatigue strength, etc).

For example, the specific heat capacity indicates how much magnetic energy is needed to raise the temperature of unit mass of the material by 1° C., while the thermal conductivity specifies how quickly the heat is transferred from the heated material to the surrounding tissues. Furthermore, the mechanical properties (e.g., elastic modulus, yield strength, fatigue/fracture properties etc.) can also be important. The mechanical properties, on the other hand, can provide a measure of the lifetime of the material, i.e., how long a device would be safe in a patient.

Disclosed embodiments include compositions of matter including particles and articles that provide reduced MRI-induced induction heating as compared to conventional high electrical conductivity metal materials, articles and devices therefrom. For example, for medical devices including for cardiac and neurostimulator leads for implantable medical devices that provide enhanced MRI compatibility. For medical applications, modifying the surface to make the surface of medical components more reflective to rapidly time-varying electromagnetic fields, such as RF magnetic fields in MRI and magnetic resonance tomography (MRT), reduces induction heating of the components within the body due to eddy currents, because the incident magnetic field is more strongly reflected by such reflective surfaces as compared to the bulk (unmodified portion) of the material. For some applications, the modified surfaces as disclosed herein may also be made to be more highly absorbed surfaces as compared to the bulk of the material. Disclosed embodiments can also be used for a variety medical applications other than MRI, and non-medical applications using more highly absorbing modified surfaces including sensors, detectors, and energy-related applications including solar cells and energy harvesters.

One embodiment comprises integral composition of matters such as particles and integral articles which comprise a substrate material (M) having a bulk portion and an outer surface that is integrated with the bulk portion. The outer surface comprises a modified surface layer. The modified surface layer includes M and at least one other material (X). X is usually a metal or metal alloy.

As used herein, "integrated structures" and "integrated articles" refer to structures that have smooth transitions in composition between the bulk portion and an outer surface, that thus lack demarcation therein, such as in the case of an article having an adhesive between two layers each having different compositions. In some embodiments, M is in the form of a crystalline lattice, and X is substitutional or interstitial atoms in the lattice of M. In some embodiments, there is also a thin cladding layer of X (e.g., 5 nm to 500 nm thick) integrated to and on the modified surface layer (comprising M and X).

The modified surface layer extends in to a depth from the outer surface at least 1 nm, typically to a depth of at least 10 nm, such as 10 nm to 500 nm. The modified surface layer has a 25° C. electrical conductivity which is at least 2.5% above or below a 25° C. electrical conductivity in the bulk portion of M. Embodied as an article, the article can include a frequency selective surface (FSS)-based metamaterial comprising a plurality of modified surface portions, and the plurality of modified surface portions can be arranged to provide a resonant frequency.

BRIEF DESCRIPTION OF THE DRAWINGS

FIG. 2A depicts laser modified rectangular and/or square patches along the circumference and length of the wire, FIG. 2B depicts laser-modified circular rings along the length of the wire, and FIG. 2C depicts laser-modified one spiral or multiple spirals along the length of the wire.

DETAILED DESCRIPTION

Figure 1:
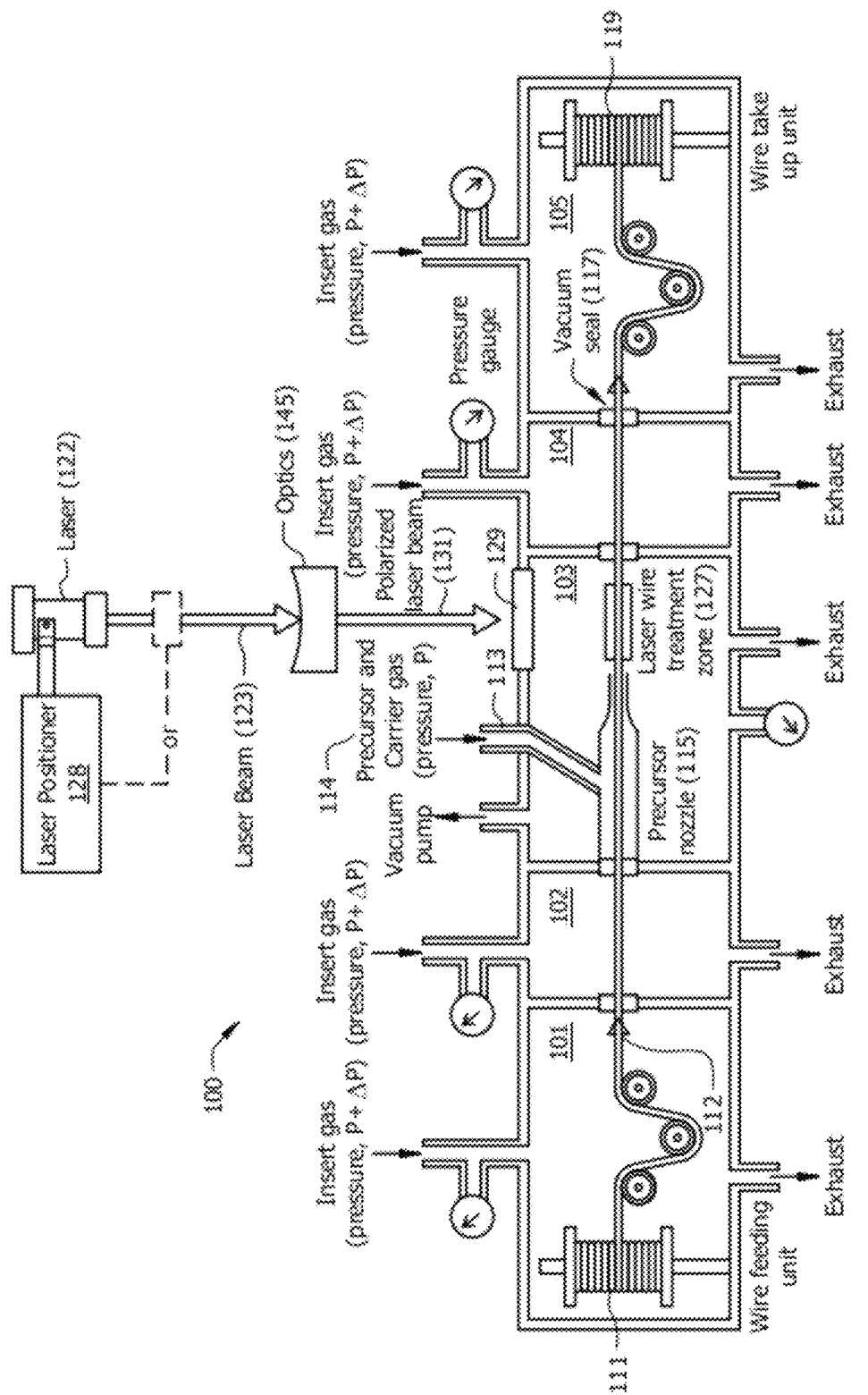
FIG. 1 shows a depiction of an example gas-tight feed through material processing system for laser treatment of wires that includes a sealed chamber comprising five compartments including a laser processing compartment, according to an example embodiment.

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Disclosed embodiments include reflective surface fabrication by diffusion processing. In one disclosed embodiment, an article is formed by modifying the outer surface of a medical grade material (M) to form a modified surface layer by incorporating another material in the outer surface that comprises a metal (X) into M. X is usually a metal or metal alloy.

The material can comprise particles or an article can be in the form of a wire, sheet, plate and rod. In the case of an article, the incorporation of X in the outer surface of the material can be localized to form a pattern, or be global across the outer surface. X can be selected so that the modified surface layer of the article has 2.5% higher or 2.5% lower 25° C. electrical conductivity as compared to the 25° C. electrical conductivity of bulk portion of M. Disclosed materials and articles can be used for leads for medical implants, stents and surgical tools, among other articles and devices.

In one embodiment, the medical component has a modified surface layer that provides a more electrically resistive surface so that the ability of rapidly varying magnetic fields to create eddy currents in the component is reduced, because the electrons are tightly bound to the nuclei in such electrically resistive materials. A "medical component" is defined herein as being formed from a biocompatible material and being part of a medical implant, such as the lead wire of pacemaker, or a medical tool. Medical tools can include needles, knives, tongs, and other items that have the potential for surgical applications in MRI environments. Although M generally comprises a metal or metal alloy, in certain embodiments M may comprise non-metals, such as ceramics or polymer comprising composite materials including an alloy, or a combination of these materials.

When M comprises a metal, M generally comprises a nonmagnetic metal or nonmagnetic metal alloy, such as Ti or Ta in the case on metals, or MP35N, for example, in the case of metal alloys MP35N (or Co—Cr—Ni—Fe—Mo—Mn alloy) is known as ELGILOY®, from Elgiloy, Ltd. MP35N is nonmagnetic, and possesses a unique combination of ultrahigh tensile strength (up to 300 ksi [2068 MPa]), good ductility and toughness, and excellent corrosion resistance. MP35N is commonly used for medical lead conductors, such as for cardiac pacemakers.

As noted above, X can include a metal or metal alloy. For example, X can comprise one or more of Pt, Pd, Au, Ag, Cu or Al.

M can be surface modified to provide a modified surface layer up to a desired depth, such as on the order of the skin depth, using one or multiple laser beams because of their localized heating capability due to available small spot sizes. Lasers allow precise control in delivering energy to a workpiece (comprising material M) and, therefore, a small thickness beneath the surface of the workpiece can be heated with lasers without significantly heating the entire (bulk portion) workpiece. The workpiece can be irradiated with either focused or unfocused laser beams.

Disclosed metal precursors, which are generally metal organic compounds including the metal X, can be used to incorporate X into M to form modified surface layers as described below. The precursor molecules can be decomposed chemically at laser-heated spots due to pyrolytic decomposition or photolytic decomposition, or a combination thereof, to form atoms of X. Some or all of the X atoms can be subsequently diffused into M to increase (or decrease) the reflectivity of the surface including M for the incident magnetic field of interest. X is typically in a range of 0.05 to 10 atomic % of the modified surface layer. The concentration of X may be low enough so that a material (M) that already satisfies FDA requirements, modified as disclosed herein to include X will not be required to undergo another FDA approval.

Since the workpiece (particles or article) can be locally heated to very high temperatures (close to its melting temperature) with lasers in a controlled manner, the diffusion coefficient of the solute atoms (X) has been unexpectedly found to be up to about five orders of magnitude higher than that obtained under thermal equilibrium heating conditions. As defined herein "thermal equilibrium heating conditions" refer to the situation where the entire workpiece is at the same temperature and the temperature does not vary spatially within the workpiece with time. Disclosed laser surface diffusion processes thus enable introducing far more atoms of X into M than what can be achieved in conventional equilibrium heating processes, including more X per unit volume, and in some cases a deeper diffusion depth. Accordingly, the reflectivity of M can be correspondingly increased more by disclosed laser diffusion processes as compared to conventional equilibrium heating processes.

Laser polarization is another parameter that can be used to enhance the diffusivity of X in M. The polarization described herein represents the line or curve traced by the tip of the electric field vector of the radiation from a laser on a plane perpendicular to the direction of propagation of the radiation. The diffusivity of X depends on the vibrational frequencies of the M atoms. In conventional heating and even in unpolarized laser heating, the atoms vibrate randomly resulting in phonons with randomly varying energy. Also the phonons propagate inside the material incoherently and in random directions. These randomly moving incoherent phonons in M can impede the migration of X from one point to another point in M and, therefore, reduce the diffusivity of X. In this embodiment polarization can be used to control the direction of motion of the phonons and, thereby, affect the diffusivity of X in M, generally to increase the diffusivity of X in M.

The laser beam is generally a polarized beam, and can be linearly, circularly or elliptically polarized, or a combination thereof. Generally the beam emitted from a laser system is unpolarized. Polarized beams can be formed from the unpolarized beam using one or more polarizers, such as based on birefringent materials including a Wollastom prism, Rochon prism and Sénarmont prism, or using other anisotropic material-based optical elements such as a Pockels cell. Depending on the microstructural properties of M such as the grain size, crystal structure, lattice parameters and preferred orientation of the crystalline planes, and the properties of X such as the electrochemical, thermomechanical, electromagnetic and physical properties, the diffusivity can be enhanced using an appropriate polarization.

Disclosed embodiments also include new material processing apparatus which provide laser treatment for workpieces, such as particles or wire materials comprising a metal substrate material having a bulk portion and an outer surface, wherein the processing modifies the outer surface by forming a modified surface layer that is modified by adding another material(s) X relative to the bulk portion (M) over at least a portion of the outer surface.

FIG. 1 shows a depiction of an example gas tight feed through material processing system 100 for laser treatment of articles shown as a wire 112 that includes a chamber comprising five sealed compartments 101-105 having vacuum seals 117 between the respective compartments. Since the process implemented generally utilizes a metall-organic compound as a precursor that may be toxic and/or pyrophoric, processing system 100 is designed to carry out the laser diffusion process safely, and comprises a sealed chamber, that in one embodiment comprises the five sealed compartments depicted in FIG. 1. Vacuum pumps are not shown, but are present to provide the exhaust flows shown out from the various compartments 101-105.

A wire feeding spool 111 is in compartment 101 and the wire 112 is collected with a take up spool 119 in compartment 105 after the wire 112 passes through two inert gas-filled buffer compartments 102 and 104, and a laser processing compartment 103. The wire 112 comprises material M, and generally receives processing before being placed in compartment 101 to remove surface impurities, such as removal of thin metal oxide layers.

The wire 112 (or other material being processed) may comprise a single material M, or a material comprising a substrate cladding comprising M over a support. Laser processing described below can be subsequent to wire extrusion, where the wire has been co-extruded from at least two materials, such as a substrate cladding comprising M over and integral to a support comprising another material. In laser processing compartment 103, the precursor gas or vapor together with a carrier gas (e.g., argon) 114 is delivered via an inlet 113 to a precursor nozzle 115, and the atoms of X to be introduced into the wire 112 are generally provided by using a precursor gas comprising a metallorganic compound including X. Metallorganic compounds are generally toxic and pyrophoric. The laser processing compartment 103 allows containing both the pre-processed and post-processed material M under inert or reactive conditions, and thus enables isolating the material M from ambient air completely. Processing system 100 also enables batch or continuous processing of materials such as wire 112, or particles.

The modified surface layer is formed in laser processing compartment 103. In some embodiments, there is also a thin cladding layer of primarily atoms of X (defined as >50% of the atoms), being e.g., 5 nm to 500 nm thick, formed on the modified surface layer. The laser irradiating and/or the partial pressure of the precursor gas may be used as variables to control whether or not a thin cladding layer of primarily X is formed on the modified surface layer, and its thickness. For example, lower partial pressures of the precursor gas, such as about <100 mTorr, may only form the modified surface layer, while higher partial pressures of the precursor gas, such as about 500 mTorr, or more, may be used to also form the thin cladding layer of primarily atoms of X on and integrated with the modified surface layer. For example, the thin cladding layer of primarily atoms of X can include 80 to 100 atomic % X (with the balance, if any, being M), while the modified surface layer can include 5 to 10 atomic % X, with the remainder being M.

The vacuum pumps provided generally provide at least a rough vacuum (e.g., about 1 mTorr) in compartments 101-105 when no precursor or carrier gas is flowing. With precursor gas or vapor together with carrier gas 114 flowing the pressures in compartments 101-105 can be kept at around 0.1 to 1 atmosphere (atm). During operation, compartments 101-105 can be maintained at a slightly higher pressure (e.g., 1.05 atm) as compared to the pressure (e.g. 1 atm) in the laser processing compartment 103. The buffer compartments 102 and 104 enable holding and removing any precursor gas or vapor and any chemical reaction products that might otherwise leak into compartments 102 and 104 from laser processing compartment 103.

The carrier gas can be an inert or non-reactive gas (e.g., argon or nitrogen), or a reactive gas that enhances the chemical decomposition of the precursor molecules at the surface of the wire 112, or a combination thereof. The precursor flow rate and the precursor nozzle 115 can be designed to improve the adsorption of the precursor molecules on the surface of the wire 112, and the remaining precursor molecules can exit the precursor nozzle 115 with appropriate velocity and flow direction to create a precursor shroud around the wire 112 in the laser-wire interaction (laser wire treatment) zone 127.

Processing system 100 is also shown including optics 145 which produces a polarized laser beam 131. Optics 145 can receive an unpolarized (or randomly polarized) laser beam 123 from laser 122 of Gaussian irradiance distribution and transform it into a polarized laser beam 131 of uniform or any other irradiance distribution and simultaneously focus the beam. The polarized laser beam 131 can have linear, circular, or azimuthal polarization, or any other polarization depending on the design of the optics 145. Laser positioner 128 is a computer controlled device that automatically controls the position of the laser beam 123 to produce desired patterns (e.g., such as to form the frequency selective surface (FSS) described below). Laser positioner 128 can comprise a mechanical system (e.g., x-y scanner), or an electronic scanning system in the path of the laser beam 123, such as based on an acousto-optic device (e.g., Acousto-Optical Tunable Filter (AOTF) or AO deflector).

Laser processing compartment 103 includes a window 129 that transmits the polarized laser beam 131 to allow laser processing in laser processing compartment 103. The adsorbed precursor molecules decompose due to chemical reactions at the laser-heated surface of the wire 112 in the laser wire treatment zone 127, and the diffusant atoms X and other reaction products are produced. As the reaction products move away from the laser wire treatment zone 127, the precursor shroud supplies the precursor molecules to the surface of the wire 112 to continue the chemical reactions for producing the diffusant atoms X continuously. At least a portion of the X atoms subsequently diffuse into the outer surface of the wire 112.

Thermal stresses might develop in the wire 112 due to laser heating in the laser wire treatment zone 127. These stresses can be relieved by heating the wire in laser processing compartment 103 or buffer compartment 104 after the laser wire treatment zone 127, using one or more laser beams of appropriate irradiance profiles. To remove the reaction products and any residual precursor molecules from laser processing compartment 103, a steady flow pattern can be established in this compartment using one or more inlet ports to deliver inert gases to the laser processing compartment 103 and using one or more exhaust ports coupled to a vacuum pump to expel the gas mixture. This process can enable maintaining a steady pressure in laser processing compartment 103 during processing. Similarly, as noted above, the compartments 101, 102, 104 and 105 are generally equipped with exhausts coupled to a vacuum pump to release excess gases in order to maintain steady pressures.

Optics 145 provides the functions of polarization, non-uniform (Gaussian) to more uniform intensity distribution, and focusing, referred to herein as "beam shaping optics". Optics 145 can receive the unpolarized (or randomly polarized) laser beam 123 of Gaussian irradiance distribution and transform it into a polarized laser beam 131 of uniform or any other irradiance distribution and simultaneously focus the beam. The transformed beam can have linear, circular, azimuthal or any other polarization depending on the design of the single optical element.

Disclosed embodiments also include methods for articles having reflective surfaces by forming metamaterial structures. Metamaterials comprise periodic structures. An electromagnetic metamaterial affects electromagnetic waves by having structural features which are smaller than the wavelength of the radiation to be processed.

The resonant nature of metamaterials results in frequency dispersion and narrow bandwidth operation where the center frequency is fixed by the geometry and dimensions of the elements comprising the metamaterial. Disclosed embodiments include frequency selective surface (FSS) based metamaterials. A FSS can be fabricated as planar 2-dimensional periodic arrays of metallic elements with specific geometrical shapes, or can be periodic apertures in a metallic screen. The transmission and reflection coefficients for these surfaces are dependent on the frequency of operation and may also depend on the polarization and the angle of the transmitted electromagnetic wave striking the material or angle of incidence.

As noted above, time-varying magnetic fields produce eddy currents and associated electric fields in a metal material. By forming electrically conductive or resistive structures or a combination thereof, such as by using processing system 100, the flow of currents on the surface of the article can be controlled as in electrical circuits. Using processing system 100, selective metamaterial structures can be formed by using appropriate lenses or diffractive optics, or a combination thereof, to focus the laser beam to produce a very small spot size, which is smaller than or equal to the size of the required metamaterial features. The focused laser spot can be computer controlled to be directed to arrive at only selected regions on the wire surface, and the wire 112 can thus become surface modified only where the laser interacts with the outer surface of the wire 112.

Metamaterial structures can modify the resistance, capacitance and/or inductance at the surface of the material, and in one embodiment creates a frequency control circuit having a resonant frequency that can be set based on a desired RF frequency to reduce the absorption of the incident field and thereby decrease the induction current. Design of disclosed metamaterial structures is generally computer-aided, such as by using an electromagnetic (EM) simulator. For example, one EM simulation tool is HFSS by Ansoft Corporation which uses the Finite Element method of solution.

The visibility of the material M in an MRI environment can also be enhanced as a result of these structures. The disclosed ability to modify the electrical resistance, capacitance and/or inductance at the surface of the material is in such a way that the reflectance of the surface increases for the incident field, which can enhance the MRI visibility of the material.

Interventional MRI is a technology used to MRI image inside a patient during surgery. The enhanced MRI visibility embodiment can be used for surgical tools (e.g., needles) used during such surgery and/or the actual implanted articles to aid in MRI guided surgery. MRI guided cardiac surgery and MRI guided brain surgery are particular examples.

The geometry of the periodic metamaterial structures can be designed (e.g., using an EM simulator) depending on the material's properties and the frequency of the incident field. As described below, FIGS. 2A-C and FIG. 3A show a few example metamaterial structures formed on wires. The concentration of the other material X can be varied in the metamaterial structures, which allows producing structural elements having different resistances and impedances. The distance between adjacent structural elements in the FSS can be varied to produce different capacitances and inductances. By varying these electrical properties, the resonant frequency of the electrical network formed by the metamaterial structure can be modified.

Figure 2A:
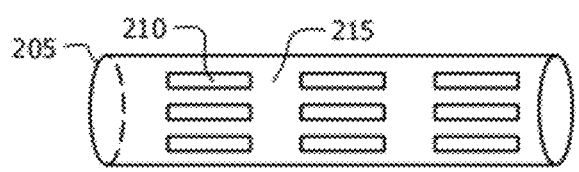
FIGS. 2A-C depict resulting articles from fabrication of a variety of metamaterial structures on wires, according to example embodiments.
Figure 2B:
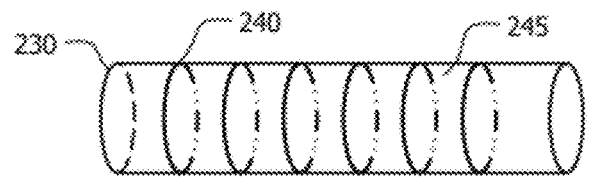
Figure 2C:
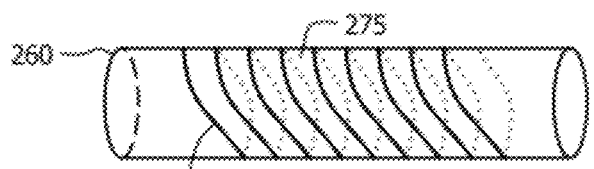

Three types of example metamaterial structures on the outer surface of wires, shown as rectangular, circular and spiral, are depicted in FIGS. 2A-C respectively. In these embodiments the integral outer surface is a modified surface layer that comprises a patterned surface layer comprising a plurality of modified surface portions and a plurality of un-modified surface portions. In FIG. 2A the modified surface layer 205 includes modified surface portions 210 which are along the circumference and length of the wire and un-modified surface portions 215. In FIG. 2B the modified surface layer 230 includes modified surface portions 240 which are along the length of the wire and un-modified surface portions 245. In FIG. 2C the modified surface layer 260 includes modified surface portions 270 which are along the length of the wire and un-modified surface portions 275.

Figure 3A:
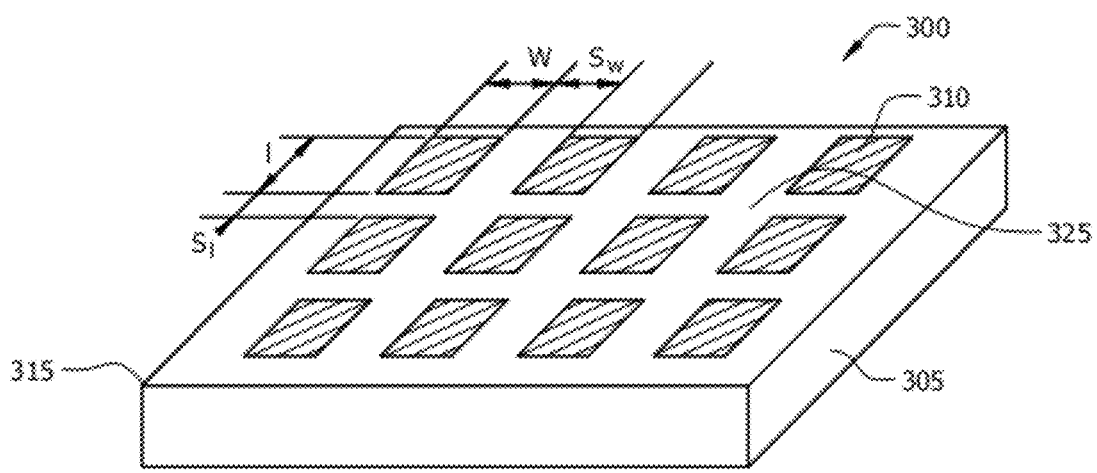
FIG. 3A depicts results from fabrication of metamaterial structures in materials having planar surfaces such as materials of rectangular geometry metamaterial structures, according to example embodiment.

An article 300 comprising a rectangular metamaterial structure on a planar surface is shown in FIG. 3A built on a substrate 305 which comprises M. The modified surface layer 315 includes modified surface elements 310 shown in FIG. 3A that comprise M and X which have a width (w), length (l), and are shown spaced from one another $S_w$ in the width direction and $S_l$ in the length direction by un-modified surface portions 325. The modified surface elements 310 can be formed using laser irradiation provided by processing system 100 as described above.

Figure 3B:
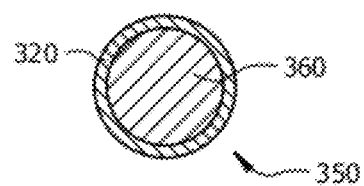
FIG. 3B shows a surface modified particle having a bulk portion comprising a material M and an outer surface integrated to the bulk portion comprising a modified surface layer having M and X, according to example embodiment.

FIG. 3B shows a surface modified particle 350 having a bulk portion 360 comprising a material M and a modified surface layer 320 integrated to the bulk portion comprising both M and X. The modified surface layer 320 extends to a depth from the outer surface at least 1 nm.

Figure 4:
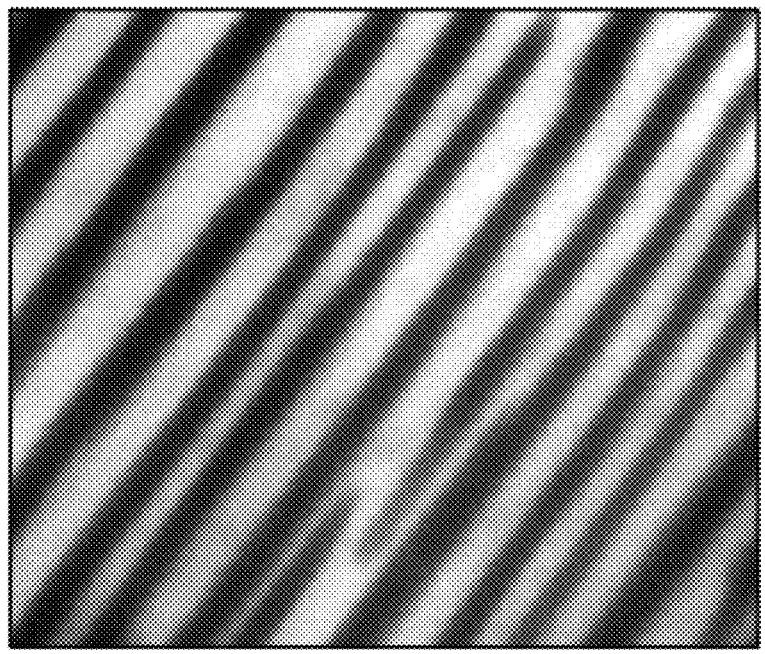
FIG. 4 shows a scanned image of a disclosed article having a modified surface layer including lamellar nano- and micro-structures that can be used to form a modified surface layer having modified resistance, capacitance and/or inductance in order to reduce the induction current based on the concept of resonator circuits.

FIG. 4 shows a scan image of a disclosed article having a modified surface layer including lamellar nano- and microstructures. The processing system 100 shown in FIG. 1 can be used to fabricate these and related structures.

Disclosed embodiments also include the fabrication of patterned glassy structures to reduce induction heating. Metallic glasses, which are amorphous alloys of binary or multiple components, can be formed due to rapid cooling or by frustrating crystallization thermodynamically or spatially. Glassy metals have very high electrical resistance which make them suitable for reducing induction heating in electric transformers.

Figure 5:
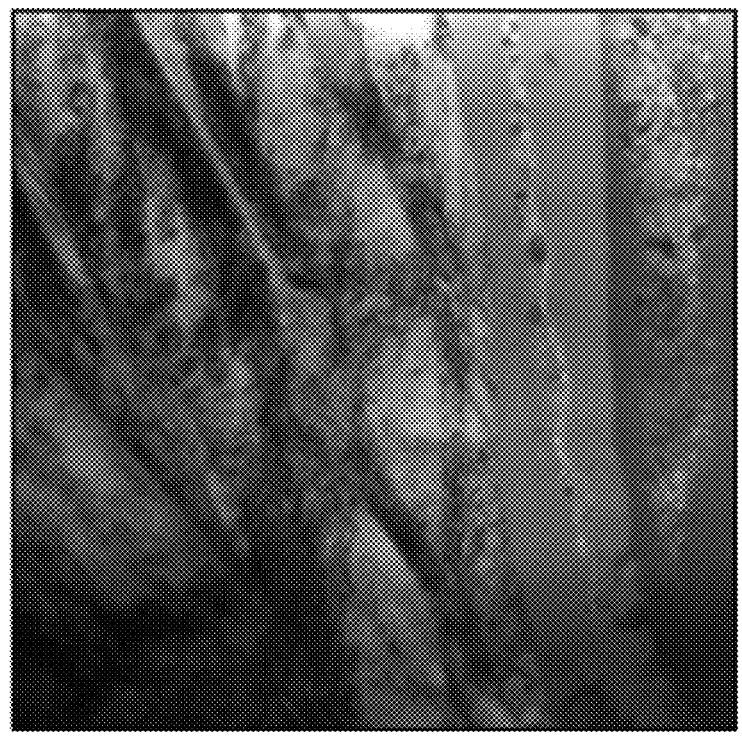
FIG. 5 shows a scanned image of a disclosed article having a modified surface layer including glassy nano- and micro-structures in metals that can control the level of cystallinity in the material and reduce the induction current much in the same way as in transformer cores.

FIG. 5 shows a scan image of a disclosed article having a modified surface layer including glassy metal. Glassy metal is also known as amorphous metal and metallic glass. Glassy metals are solid metallic material, usually an alloy, with a disordered atomic-scale structure, thus being glasses. Glassy nano- and micro-structures can be created in a pattern so that the flow of eddy currents is hindered without altering the entire surface. Glassy metals can be produced in metals by methods disclosed herein to control the level of cystallinity in the material. In one such embodiment, element X can be selected so as to break the order of atoms in substrate M from being crystalline to making them non-crystalline or glassy. Such glassy structures can affect the response of the material to electromagnetic waves, time-varying electric fields and time-varying magnetic fields, and reduce the induction current and consequently the induction heating much in the same way as in transformer cores.

Various alloying elements (X) can be diffused into M in sufficient concentration by the above-described laser surface diffusion process to tailor the level of cystallinity. In addition to alloying considerations, rapid heating and fast cooling, which is inherent in laser processing, can be utilized to melt a thin layer of the material and cool rapidly to form glassy nano- and micro-structures at the surface of M. Similarly, metallic glasses can be fabricated in the form of metamaterial structures at the surface of M by the above-mentioned metamaterial fabrication technique to tailor the electromagnetic properties of the surface, which will affect the response of M to incident electromagnetic waves and fields.

Disclosed embodiments include embodiments that improve visibility of implants in MRI environments.

Implants, such as stents and bone-repairing fixtures (metal sheets and screws), are widely used in modern health care. However, the generation of imaging artifacts of such implants in MRI environments can be a serious impediment in using the MRI to its full potential for advanced clinical procedures and non-invasive health diagnosis.

Surfaces can be tailored at strategic locations of the implants by the above-disclosed techniques to improve visibility as well as eliminate imaging artifacts. For example, strategic locations can be a few regions near the ends of the material or a few isolated regions along the length of the material or a combination thereof. These selected locations can be modified by diffusion of X into M to increase the reflectance of the material for enhanced visibility. Glassy structures or metamaterial structures or lamellar structures or a combination thereof can also be produced at the locations to increase the reflectance for improved visibility. Conversely, even the absorption can be increased to provide contrast in the image or a combination in different regions of the implant.

The modified regions of the implants or materials can interact differently with the magnetic field used in MRI, and can be used by the MRI system to display the images of the modified spots of the implants. The processing can be localized so that the image can define the boundary of the implant as described above. In another embodiment, the entire surface of the implant can be modified to eliminate artifacts (e.g., a stent showing up as globule as opposed to being able to see inside it for restenosis).

Example medical devices or portions thereof that can benefit from disclosed embodiments include, but are not limited to, those which are coupled to a power supply such as a battery and are current carrying such as cardiac leads (e.g., for pacemaker devices), neuro-stimulator leads (for neuro-stimulator devices), and non-current carrying such as clips, staples, markers, stents catheters, guide wires, orthopedic implants, cochlear implants, and valves.

Medical devices methodologies can also be engineered based on the above disclosed principles. Targeted heating using FSS-based resonance can be used to destroy tumors or cancerous cells. This is analogous to targeted radiation therapy but uses less damaging thermal heating. For example a laser doped needle can be inserted into tumorous or cancerous tissue. The needle can then be subjected to an MRI scan thereby causing it to heat up and destroy the tumor in a localized manner.

Disclosed embodiments also include absorptive surface fabrication for different wavelengths in the electromagnetic spectrum. Much of the above-disclosure relates to techniques, microstructures and nanostructures to create reflective surfaces for which one of the many possible applications is the reduction of induction heating. This embodiment instead can be used for creating absorptive surfaces to selectively increase absorption of electromagnetic waves in certain wavelength ranges for applications including sensors, detectors, photovoltaic cells and energy harvesting devices.

One or more elements (X) can be diffused into material M by the above-mentioned laser surface diffusion process to lower its electrical conductivity and increase its absorption coefficient for electromagnetic waves of a given wavelength. The elements can also be diffused into selected regions of the material M to modify other properties, such as resistance, resistivity, capacitance, inductance, electron mobility, permittivity, permeability, impedance and electron density in order to increase the absorbance of M. These properties can also be tailored by fabricating metamaterial structures as well as lamellar nanostructures and microstructures at the surface of M to increase its absorbance for a given wavelength. Examples of modified surfaces with increased absorbance are shown in FIGS. 2A-C and FIGS. 3A-5 described above. In the case of metamaterial structures with increased absorbance, the composition of each structural element, such as the concentration of X, and the distance between the adjacent elements (e.g. modified surface elements 310) can be different so that the resonant frequency of the electrical network formed by the elements is in phase with the frequency of the incident field. This type of phase-matched surfaces will enhance the absorbance. For glassy structures and lamellar structures, the material composition and the distance between the patterns can be varied to produce phase-matched surfaces for enhanced absorption. In the previous several examples described above where the absorbance is reduced, the surfaces can be designed that the resonant frequency of the electrical network formed by the elements is out of phase with the frequency of the incident field. This type of phase-mismatched surfaces can reduce the absorbance.

Figure 6A:
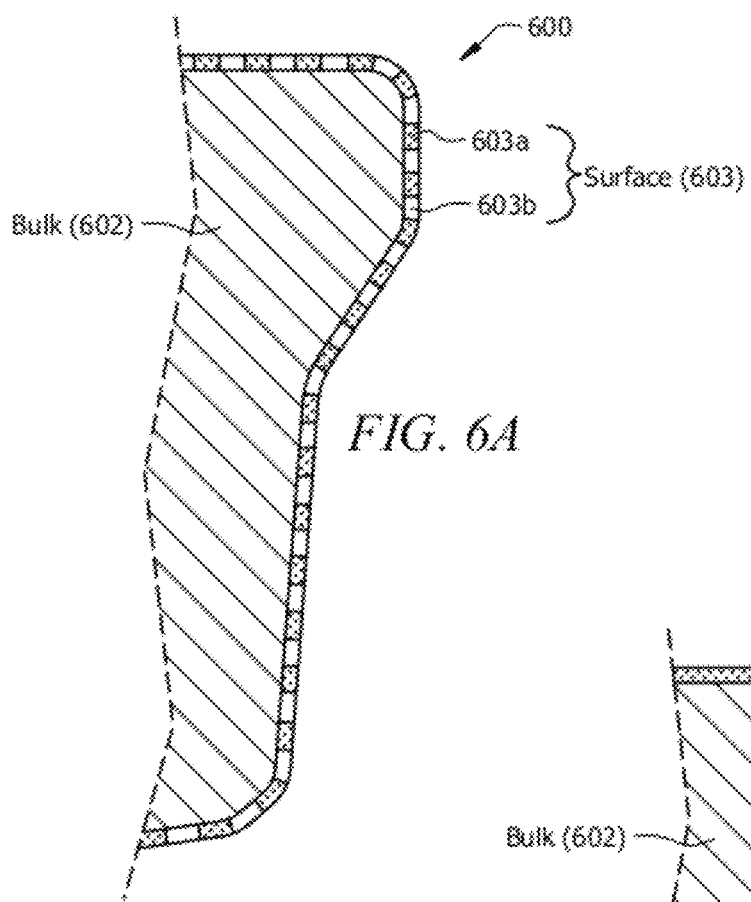
FIG. 6A is a schematic cross-sectional view of portion of a medical article having a modified surface layer formed by disclosed surface modification of materials for tailoring responses to electromagnetic fields, according to an example embodiment.

FIG. 6A is a schematic cross-sectional view of portion of a medical article 600 having a modified surface layer formed by disclosed surface modification of materials for tailoring responses to electromagnetic fields, according to an example embodiment. The medical article can be current carrying or non-current carrying. Current carrying medical articles can comprise pacemaker devices or neuro-stimulator devices that include current carrying wires. Non-current carrying articles can comprise a surgical needle, clip, staple, marker, stent catheter, guide wire, orthopedic implant, cochlear implant, or a valve.

The medical article 600 comprises a substrate having a bulk portion 602 having material (M) and a modified surface layer 603 having a plurality of modified surface portions 603*a* having M and X which are separated by un-modified surface portions 603*b* having M but not X. In one embodiment surface layer 603 provides a metamaterial structure analogous to that shown in FIG. 3. The modified surface portions 603*a* extend in to a depth from the outer edge of the surface layer 603 of at least 1 nm. Modified surface portions 603*a* have a 25° C. bulk electrical conductivity that is at least 2.5% above or below a 25° C. bulk electrical conductivity of M.

Figure 6B:
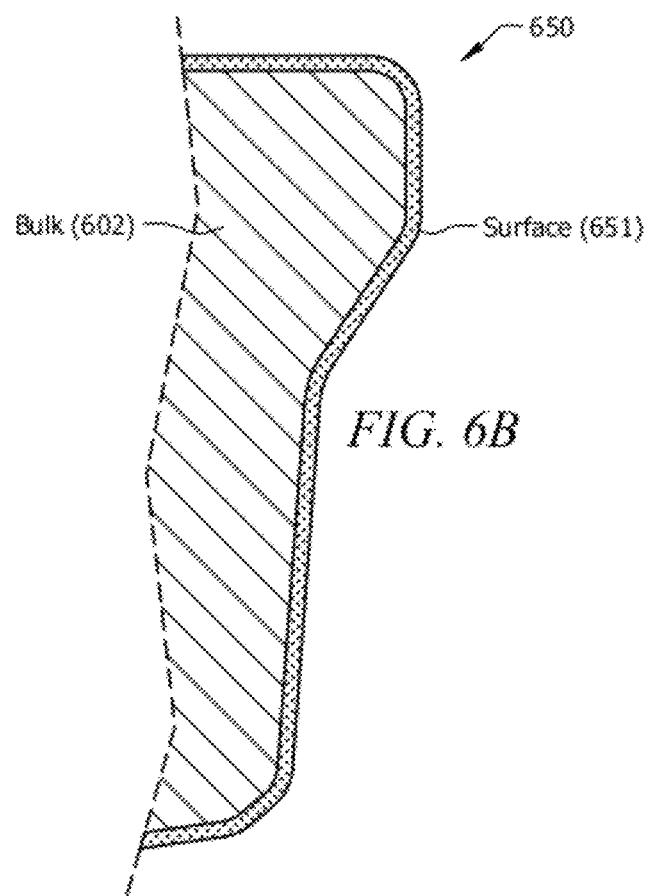
FIG. 6B is a schematic cross-sectional view of portion of a medical article having a uniformly modified surface layer formed by disclosed surface modification of materials for tailoring responses to electromagnetic fields, according to an example embodiment.

FIG. 6B is a schematic cross-sectional view of portion of a medical article 650 having a uniformly modified surface layer 651 formed by disclosed surface modification of materials for tailoring responses to electromagnetic fields, according to an example embodiment. Modified surface layer 651 is a uniform modified and is thus unlike the modified surface layer 603 of medical article 600 which includes un-modified surface portions 603*b*.

Figure 7:
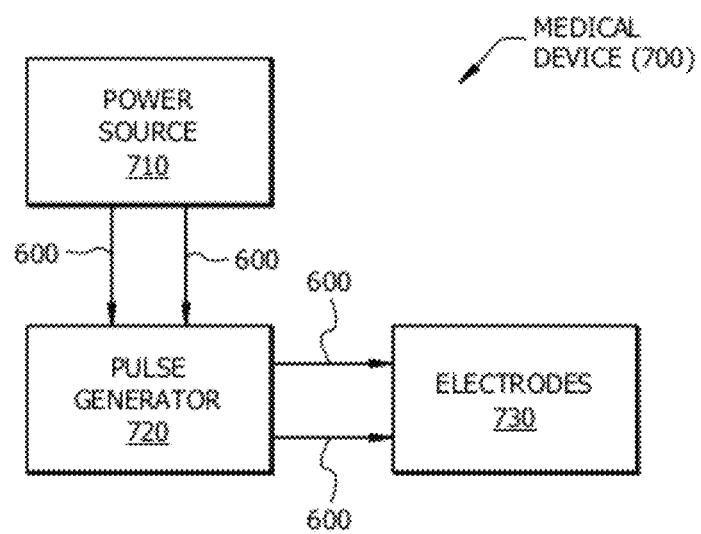
FIG. 7 is a simplified block diagram of a medical device that includes current carrying wires shown provided by a disclosed medical article, and optionally also an electrode lead system provide by a disclosed medical article, according to an example embodiment.

FIG. 7 is a simplified block diagram of a medical device 700 that includes current carrying wires shown provided by medical article 600, and optionally an electrode lead system 730 provide by medical article 600. Medical device 700 includes a power source block such as a battery 710, an electrical pulse generator block 720, and an electrode lead system block 730. The respective blocks are electrically connected to one another by medical article 600 embodied as electrical wiring. Medical device 700 can comprise a pacemaker device or neuro-stimulator device.

With regard to disclosed applications for sensors, gases as well as other materials (solids and liquids) emit radiation and these emission spectra reveal characteristic spectral wavelength for each material. The tip of a thermocouple can be tailored by the above-mentioned nanostructure and microstructure modification techniques to selectively absorb the radiation of this characteristic wavelength. The absorption can cause heating of the tip, resulting in a voltage or current signal as in typical thermocouples. Just the presence of a signal from a wavelength-specific sensor tip will enable determining the identity of the gas, and the magnitude of the signal can be used to determine the concentration of the gas with proper calibration of the sensor. This approach can also be used for identifying and determining the concentration of liquid droplet suspension and solid particulates in gases.

Another embodiment of this sensor principle is radiation detection and imaging. Bolometers are used as uncooled detectors in a certain wavelength (8 μm-10 μm) range for imaging applications. In such detectors, the incident radiation heats up the detector element and the resistance of the detector element changes as a function of its temperature. This effect changes the current and voltage in an electrical circuit connected to the detector element. The changes in the current or voltage signal are used for constructing the image of an object based on the amount of radiation received by the detector from the object. The material (detector element) for such detectors can be fabricated by the above-mentioned nanostructure and microstructure modification techniques to selectively absorb the radiation in a specific wavelength range, such as using FSS materials for resonance. This embodiment enables producing detector elements for various wavelength ranges in the electromagnetic spectrum.

This wavelength-specific absorption capability can be utilized for improved photovoltaic solar cells and electrical energy harvesting applications. Generally the reflectivity of all metals is very high in the visible range of the solar spectrum. The absorbance of the tip of thermocouples can be increased for this visible range by the above-mentioned material modification techniques. Such modified tips will absorb more of the solar energy and, therefore, the modified tips will be heated up more than the tips in conventional thermocouples. The hotter tips will produce more currents based on the basic operating principle of thermocouples. A large number of such modified tips can be embedded in thermally insulative structures to produce a large amount of current from the solar energy.

With regard to electrical energy harvesting from waste heat sources and conversion of ultraviolet energy to electrical energy, the spectral energy distribution of the sources can be determined to identify the dominant wavelength ranges in the radiation emitted by such sources. Based on these wavelengths, appropriate materials can be diffused into the tips of thermocouples as well as nano- and micro-structural changes can be made to the tips. The modified tips will absorb much of the incident radiation to produce more electricity than conventional thermocouples.

Another application for disclosed embodiments is for localized cell heating applications. As noted above, disclosed surface modified particles can be manufactured to have enhanced absorption at certain wavelengths. The enhanced absorption can be used to increase the heating provided by conventional uniform particles. Particles for disclosed surface modification can be provided by a number of sources, such as from sol-gel processing.

The above-described surface modification processes can be undertaken as an intermediate step during fabrication of the material, article, or device and not necessarily the final step. This allows subsequent routine processing to obtain improved mechanical properties (e.g., elastic moduli, yield strength, fatigue/fracture properties) or biocompatible properties (e.g., an oxide or protective coating) or pharmacological properties (e.g., a drug eluting coating) of the material or device.

One such embodiment is the case where laser diffusion and surface patterning of the wire is followed by a subsequent extrusion process to improve mechanical properties of the wire. Another embodiment is the case where laser diffusion and patterning of the wire is immediately followed by a laser heating process (without diffusion and patterning) to improve mechanical properties of the wire.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

We claim:

1. A method for making a metamaterial structure, the method comprising:
   providing a substrate having a bulk portion and an outer surface layer integrated to the bulk portion, the substrate comprising a first metal material and having a crystalline structure;
   performing of a first exposure of the substrate in an inert gas;
   after the first exposure, performing a chemical vapor deposition (CVD) of at least one other organometallic material in the outer surface layer of the substrate;
   laser irradiating, with a polarized laser beam, the at least one other organometallic material at a plurality of first surface portions to decompose chemically at laser-heated spots due to decomposition of the at least one other organometallic material to form at least one other metal material, the plurality of first surface portions having both the first metal material and at least one other metal material, the outer surface layer comprising a plurality of second surface portions comprising only the first metal material, the laser irradiating causing a diffusion of the plurality of first surface portions and the at least one other metal material into the substrate to a diffusion depth being in a range of 10 nm to 500 nm;

during the laser irradiating, heating the substrate; and after the laser irradiating, performing a second exposure of the substrate in the inert gas;

the at least one other metal material being distributed throughout the plurality of first surface portions of the outer surface layer with a concentration profile varying as a function of distance within the outer surface layer;

the plurality of first surface portions having a 25° C. electrical conductivity being at least 2.5% above or below a 25° C. electrical conductivity in the bulk portion;

the plurality of first surface portions and the plurality of second surface portions having a spacing and arrangement to define an electrical network, a resonant frequency of the electrical network being in phase with a frequency of an incident electromagnetic field.

2. The method of claim 1, wherein the at least one other metal material comprises Pt, Pd, Au, Ag, Cu or Al.

3. The method of claim 1, wherein the first metal material comprises a nonmagnetic metal.

4. The method of claim 3, wherein the nonmagnetic metal comprises Ti, Ta, or a MP35N alloy.

5. The method of claim 1, wherein the CVD deposits the at least one other organometallic material in a cladding layer with a thickness between 5 nm and 500 nm.

6. The method of claim 5, wherein the cladding layer is formed at a pressure greater than 500 mTor.

7. The method of claim 1, wherein the laser irradiating comprises a selectively positioning the polarized laser beam on the substrate to define the plurality of first surface portions and the plurality of second surface portions.

8. The method of claim 1, wherein the CVD comprises exposing the substrate to a precursor gas and a carrier gas.

9. The method of claim 8, wherein the precursor gas comprises at least one of argon gas and nitrogen gas.

10. The method of claim 1, wherein the laser irradiating is performed within a vacuum.

11. A method for making a metamaterial structure, the method comprising:

providing a substrate having a bulk portion and an outer surface layer integrated to the bulk portion, the substrate comprising a first metal material and having a crystalline structure;

performing of a first exposure of the substrate in an inert gas;

after the first exposure, performing a chemical vapor deposition (CVD) of at least one other organometallic material in the outer surface layer of the substrate;

laser irradiating, with a polarized laser beam, the at least one other organometallic material at a plurality of first surface portions to decompose chemically at laser-heated spots due to decomposition of the at least one other organometallic material to form at least one other metal material, the plurality of first surface portions having both the first metal material and at least one other metal material, the outer surface layer comprising a plurality of second surface portions comprising only the first metal material, the laser irradiating causing a diffusion of the plurality of first surface portions and the at least one other metal material into the substrate to a diffusion depth being in a range of 10 nm to 500 nm;

during the laser irradiating, heating the substrate; and after the laser irradiating, performing a second exposure of the substrate in the inert gas;

the at least one other metal material being distributed throughout the plurality of first surface portions of the outer surface layer with a concentration profile varying as a function of distance within the outer surface layer;

the plurality of first surface portions having a 25° C. electrical conductivity being at least 2.5% above or below a 25° C. electrical conductivity in the bulk portion;

the plurality of first surface portions and the plurality of second surface portions having a spacing and arrangement to define an electrical network, a resonant frequency of the electrical network being in phase with a frequency of an incident electromagnetic field;

the at least one other metal material comprising Pt, Pd, Au, Ag, Cu or Al;

the first metal material comprising a nonmagnetic metal.

12. The method of claim 11, wherein the nonmagnetic metal comprises Ti, Ta, or a MP35N alloy.

13. The method of claim 11, wherein the CVD deposits the at least one other organometallic material in a cladding layer with a thickness between 5 nm and 500 nm.

14. The method of claim 13, wherein the cladding layer is formed at a pressure greater than 500 mTor.

15. The method of claim 11, wherein the laser irradiating comprises a selectively positioning the polarized laser beam on the substrate to define the plurality of first surface portions and the plurality of second surface portions.

16. The method of claim 11, wherein the CVD comprises exposing the substrate to a precursor gas and a carrier gas.

17. The method of claim 16, wherein the precursor gas comprises at least one of argon gas and nitrogen gas.

18. The method of claim 11, wherein the laser irradiating is performed within a vacuum.

* * * * *